United States Patent
Hao et al.

(10) Patent No.: US 11,793,550 B2
(45) Date of Patent: Oct. 24, 2023

(54) CLAW-SHAPED PEDICLE SCREW FASTENER FOR OSTEOPOROSIS

(71) Applicant: Dingjun Hao, Shaanxi (CN)

(72) Inventors: Dingjun Hao, Shaanxi (CN); Haiping Zhang, Shaanxi (CN)

(73) Assignee: Dingjun Hao, Shaanxi (CN)

( * ) Notice: Subject to any disclaimer, the term of this patent is extended or adjusted under 35 U.S.C. 154(b) by 0 days.

(21) Appl. No.: 17/881,611

(22) Filed: Aug. 5, 2022

(65) Prior Publication Data

US 2023/0084223 A1    Mar. 16, 2023

(30) Foreign Application Priority Data

Sep. 16, 2021   (CN) .......................... 202111089461.7

(51) Int. Cl.
*A61B 17/70* (2006.01)
*A61B 17/86* (2006.01)
*A61L 27/28* (2006.01)

(52) U.S. Cl.
CPC ........ *A61B 17/7032* (2013.01); *A61B 17/864* (2013.01); *A61B 17/8685* (2013.01); *A61L 27/28* (2013.01)

(58) Field of Classification Search
CPC .............. A61B 17/7032; A61B 17/864; A61B 17/8685; A61L 27/38; F16B 19/1072; F16B 13/061
USPC ....... 606/265, 267, 270, 271, 272, 275, 301, 606/304, 308, 310, 313, 315, 316, 317, 606/319, 326, 327, 328, 99, 86 A
See application file for complete search history.

(56) References Cited

U.S. PATENT DOCUMENTS

| | | | | | |
|---|---|---|---|---|---|
| 4,760,843 | A | * | 8/1988 | Fischer | A61B 17/686 606/313 |
| 5,209,753 | A | * | 5/1993 | Biedermann | A61B 17/686 606/314 |
| 5,259,398 | A | * | 11/1993 | Vrespa | A61C 8/0025 411/413 |
| 2016/0270826 | A1 | * | 9/2016 | Marino | A61B 17/7037 |
| 2017/0354442 | A1 | * | 12/2017 | Kim | A61B 17/7032 |
| 2019/0159820 | A1 | * | 5/2019 | Geist | A61B 17/8685 |

FOREIGN PATENT DOCUMENTS

| | | | | |
|---|---|---|---|---|
| WO | WO-2013173544 | A1 | * 11/2013 | ......... A61B 17/7032 |
| WO | WO-2015095965 | A1 | *  7/2015 | ......... A61B 17/7032 |

\* cited by examiner

*Primary Examiner* — Eduardo C Robert
*Assistant Examiner* — David C Comstock

(57) ABSTRACT

A claw-shaped pedicle screw fastener for osteoporosis includes an inner screw plug and an outer screw; the outer screw includes an outer nut and an outer screw stem, a through hole is defined in and penetrates through the outer nut and the outer screw stem, the outer screw stem has a thread segment, a claw-shaped segment, and a conical segment that are provided on outside of the outer screw stem; the claw-shaped segment is made of deformable metal; the inner screw plug includes an inner nut and an inner screw stem, the inner screw stem is inserted into the through hole, and the inner screw stem is threadedly connected to the first inner thread and the second inner thread; the inner screw stem and the second inner thread are reverse thread screws relative to each other.

10 Claims, 5 Drawing Sheets

CLAW-SHAPED PEDICLE SCREW FASTENER FOR OSTEOPOROSIS

FIELD

The present disclosure relates to the technical field of surgical instruments for osteoporosis, in particular to a claw-shaped pedicle screw fastener for osteoporosis.

BACKGROUND

As the life expectancy of older adults increases, the number of patients with spinal osteoporosis continues to grow. Due to the weakening of bone remodeling ability and the decline of vertebral bone quality of these patients, the spine is prone to compression fractures, degenerative deformities, stenosis, etc., and surgical intervention is usually required. Although pedicle screws provide strong fixation for patients with normal bone mass, people with osteoporosis usually have the risk of postoperative screw pullout, loosening and displacement, due to the significant decrease of the holding force of the screw in the osteoporotic bone.

Researchers have tried to enhance the holding force of the screw in the osteoporotic bone by using bone cement to enhance screw stability. Many studies have shown that the average anti-pullout strength of pedicle screws reinforced by bone cement can reach 150-250% of that of common pedicle screws. However, with the increase of the used bone cement-reinforced screws, many complications and risks associated therewith have gradually emerged, the most common of which is bone cement leakage (the incidence reported in the literature is up to 26.2%). In addition, there is also a risk of other complications including thermal bone cement injury, pulmonary embolism, compression fractures of adjacent vertebral bodies, etc., and repair thereof is difficult.

In order to avoid the risks of various complications caused by the use of bone cement, scholars have designed and developed a new type of screws, expansion screws, to replace the screws with bone cement to enhance the holding force. After the screw of this type is placed in the vertebral body, the expansion of a part of the screw located in the vertebral body increases a contact area between the screw and the surrounding bone, and increases the density of the surrounding bone by compressing the surrounding bone, thereby significantly strengthening the anti-pullout force of the screw. Most of the early reported expansion screws have head ends thereof expanded. Recently, some scholars reported a new type of expansion screws (OsseoScrew spinal internal fixation system), and an expandable part of the screw is close to the vertebral pedicle, which is beneficial to enhance its anti-pullout strength. Compared with ordinary pedicle screws, this screw can increase the anti-pullout strength by about 30% (by about 50% in osteoporotic bones), and its stiffness and yield load are not significantly different from those of pedicle screws with common outer diameters.

Some studies have shown that the effect of the expansion screw in enhancing its fixation stability is similar to that of bone cement, but when the screw was used clinically, it was found that there were screws breaking at the pedicle. Secondly, after the screw is implanted and expanded, the surrounding bone can grow into the expansion region, resulting in difficulties in removing the screw and easily leading to large vertebral bone defects when repair of the screw is required in a later stage, and it is often necessary to lengthen the fixed segment to maintain the stability of the fixation.

SUMMARY

In order to avoid the risks of various complications caused by the use of bone cement and expansion screws, the present disclosure provides a claw-shaped pedicle screw fastener for osteoporosis. The present disclosure designs a claw-shaped pedicle spray screw fastener. After the screw fastener is placed in the vertebral body, the anti-pullout force of the screw fastener is enhanced through a claw-shaped structure of a part of the screw fastener located in the vertebral bone, and through an internal screw plug increasing the holding force of the screw fastener for the surrounding bone.

In order to achieve the above objects, the present disclosure provides the following technical solutions.

A claw-shaped pedicle screw fastener for osteoporosis, including an inner screw plug and an outer screw; the outer screw includes an outer nut and an outer screw stem, a through hole is defined in and penetrates through the outer nut and the outer screw stem, the outer screw stem has a thread segment, a claw-shaped segment, and a conical segment that are provided on outside of the outer screw stem, the thread segment has a first inner thread provided inside, the claw-shaped segment has a plurality of strip-shaped grooves provided thereon and being in communication with the through hole, and the claw-shaped segment is smooth inside; the conical segment has a second inner thread provided inside; the claw-shaped segment is made of deformable metal; the thread segment has a first outer thread provided thereon, and a thread direction of the first inner thread is opposite to a thread direction of the second inner thread; and a thread direction of the first outer thread is the same as the thread direction of the second inner thread; and the inner screw plug includes an inner nut and an inner screw stem, the inner screw stem is inserted into the through hole, the inner screw stem has a second outer thread provided thereon, the second outer thread of the inner screw stem is connected to the first inner thread, and the second outer thread is configured to have an interference with the second inner thread under an action of a twisting force provided by the inner screw stem to twist and expand the claw-shaped segment.

As a further improvement of the present disclosure, the outer screw stem is a conical structure, and the first outer thread has a decreasing pitch and an increasing thread diameter in a direction from the thread segment to the outer nut.

As a further improvement of the present disclosure, the first outer thread has a hydroxyapatite spray coating on a tail thereof.

As a further improvement of the present disclosure, the inner nut has a second wrench operating groove provided thereon.

As a further improvement of the present disclosure, a length of the inner screw stem is equal to a length of the outer screw stem minus a length of the second inner thread.

As a further improvement of the present disclosure, an operating tool is included, and the operating tool includes a locking nut and an operating rod; the outer nut has a locking groove provided thereon and has a locking thread provided inside; and the operating rod, when in use, is disposed in the locking groove, and is locked up through a threaded connection between the locking nut and the locking thread.

As a further improvement of the present disclosure, the locking nut has a first wrench operating groove provided thereon.

As a further improvement of the present disclosure, the operating rod is axially perpendicular to the outer screw.

As a further improvement of the present disclosure, the claw-shaped segment is made of pure titanium, and the thread segment is made of titanium alloy.

As a further improvement of the present disclosure, the plurality of strip-shaped grooves is uniformly arranged on the claw-shaped segment along an axial direction of the claw-shaped segment.

Compared with the related art, the present disclosure has the following beneficial effects.

The present disclosure provides a claw-shaped pedicle screw fastener for osteoporosis. The present disclosure designs a claw-shaped pedicle spray screw fastener. After the screw fastener is placed in the vertebral body, the anti-pullout force of the screw fastener is enhanced through the claw-shaped structure of a part of the screw fastener located in the bone of the vertebral body, and through the internal screw plug increasing the holding force of the screw for the surrounding bone.

BRIEF DESCRIPTION OF DRAWINGS

The drawings described herein are for explanatory purposes only and are not intended to limit the scope of the present disclosure in any way. In addition, the shapes and proportional scales of the components in the figures are only schematic and are used to help the understanding of the present disclosure, and are not intended to specifically limit the shapes and proportional scales of the components of the present disclosure. In the drawings.

DESCRIPTION OF EMBODIMENTS

Figure 1:
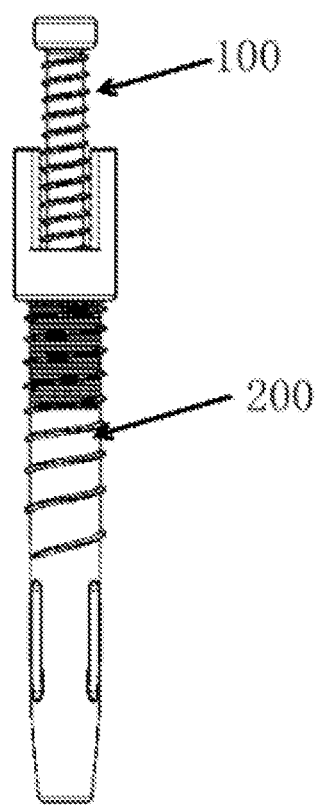
FIG. 1 is a schematic diagram of a claw-shaped pedicle screw fastener for osteoporosis.
Figure 2:
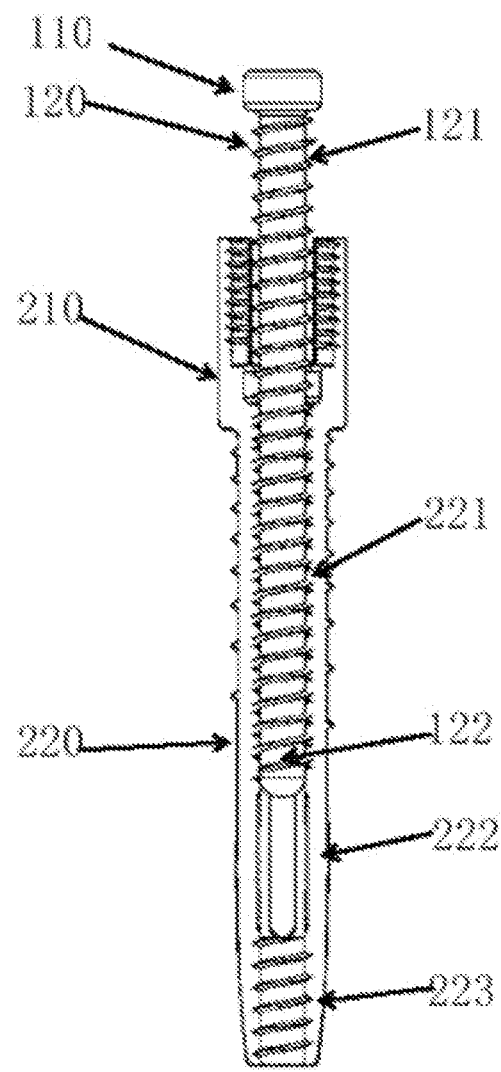
FIG. 2 is a cross-sectional view of a claw-shaped pedicle screw fastener for osteoporosis.
Figure 3:
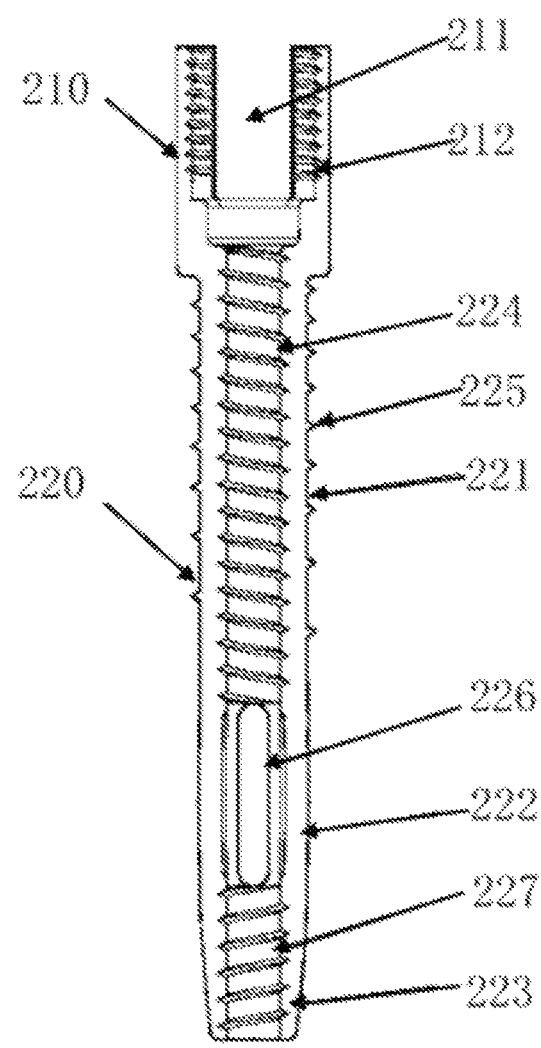
FIG. 3 is a cross-sectional view of an outer screw of a claw-shaped pedicle screw fastener for osteoporosis.
Figure 4:
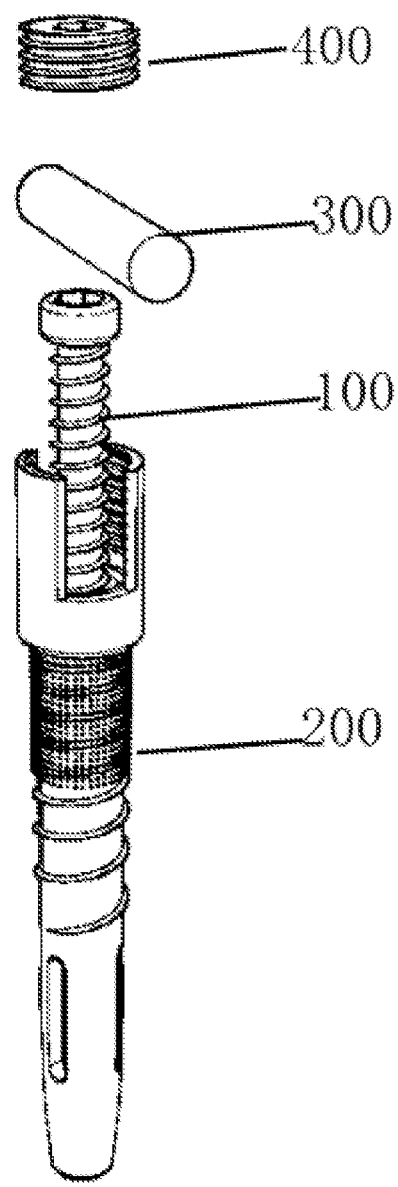
FIG. 4 is an exploded view of a claw-shaped pedicle screw fastener for osteoporosis.
Figure 5:
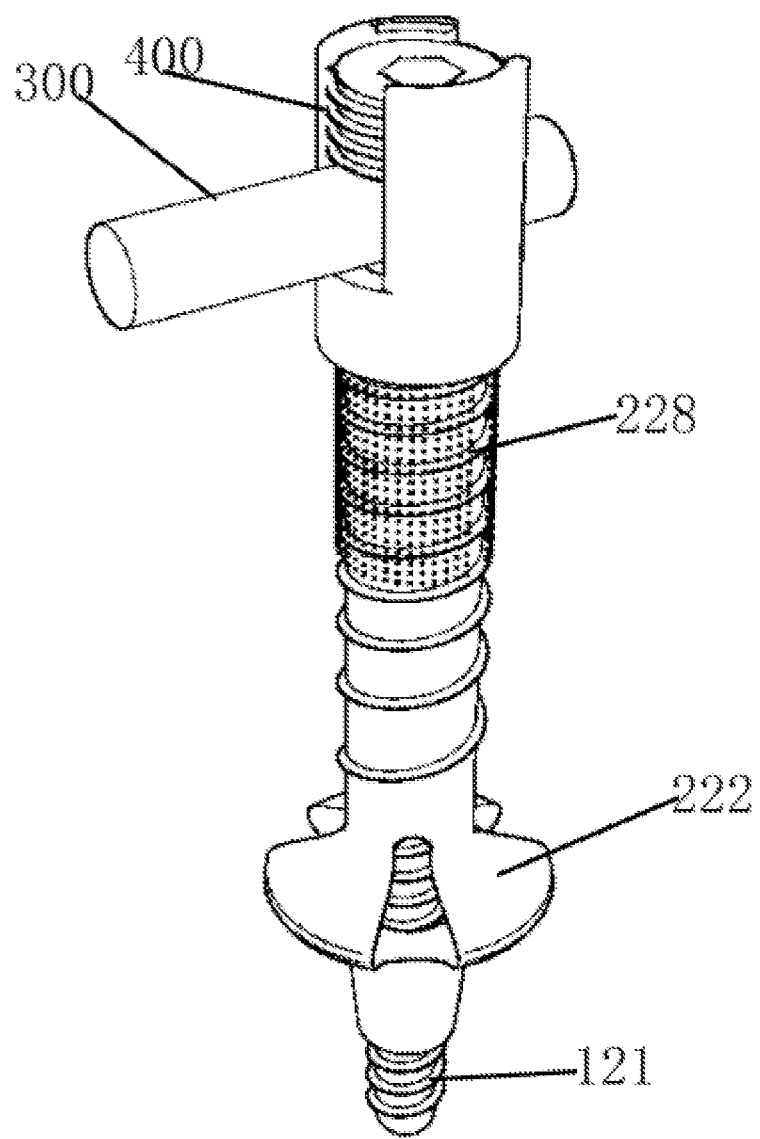
FIG. 5 is a schematic diagram of a use state of a claw-shaped pedicle screw fastener for osteoporosis.

In order to make those skilled in the art better understand the technical solutions of the present disclosure, the technical solutions in the embodiments of the present disclosure will be clearly and completely described below with reference to the accompanying drawings in the embodiments of the present disclosure. Apparently, the described embodiments are only some of the embodiments of the present disclosure, but not all of the embodiments. Based on the embodiments of the present disclosure, all other embodiments obtained by those of ordinary skill in the art without creative labor shall fall within the protection scope of the present disclosure.

It should be noted that when an element is referred to as being "disposed on" another element, it can be directly on another element, or intermediate elements may also be present. When an element is referred to as being "connected to" another element, it can be directly connected to another element, or intermediate elements may also be present. The terms "vertical", "horizontal", "left", "right" and similar expressions used herein are for the purpose of illustration only and do not represent a unique embodiment.

Unless otherwise defined, all technical and scientific terms used herein have the same meaning as commonly understood by those of ordinary skill in the art to which this disclosure belongs. The terms used in the description of the present disclosure are for the purpose of describing specific embodiments only, and are not intended to limit the present disclosure. As used herein, the term "and/or" includes any and all combinations of one or more of the associated listed items.

The present disclosure provides a claw-shaped pedicle screw fastener for osteoporosis, including an inner screw plug 100 and an outer screw 200; the outer screw 200 includes an outer nut 210 and an outer screw stem 220, a through hole is defined in and penetrates through the outer nut 210 and the outer screw stem 220, the outer screw stem 220 has a thread segment 221, a claw-shaped segment 222, and a conical segment 223 that are provided on outside of the outer screw stem 220, the thread segment 221 has a first inner thread 224 provided inside, the claw-shaped segment 222 has a plurality of strip-shaped grooves 226 provided thereon and being in communication with the through hole, and the claw-shaped segment 222 is smooth inside; the conical segment 223 has a second inner thread 227 provided inside; the claw-shaped segment 222 is made of deformable metal; the thread segment 221 has a first outer thread 225 provided thereon, and a thread direction of the first inner thread 224 is opposite to a thread direction of the second inner thread 227; and a thread direction of the first outer thread 225 is the same as the thread direction of the second inner thread 227; and the inner screw plug 100 includes an inner nut 110 and an inner screw stem 120, the inner screw stem 120 is inserted into the through hole, the inner screw stem 120 has a second outer thread 121 provided thereon, the second outer thread 121 of the inner screw stem 120 is connected to the first inner thread 224, and the second outer thread 121 is configured to have an interference with the second inner thread 227 under an action of a twisting force provided by the inner screw stem to twist and expand the claw-shaped segment 222.

The principle is that a reverse thread of a reverse thread screw will move upward when the inner screw plug 100 is screwed in, thereby squeezing and expanding the claw-shaped segment 222.

As a preferred embodiment, the outer screw stem 220 is a conical structure, and the first outer thread 225 has a decreasing pitch and an increasing thread diameter in a direction from the thread segment 221 to the outer nut 210.

Preferably, the first outer thread 225 has a hydroxyapatite spray coating 228 on a tail thereof.

Preferably, a length of the inner screw stem 120 is equal to a length of the outer screw stem 220 minus a length of the second inner thread 227. Such a design enables the inner screw plug 100 to be stuck on the top of the second inner thread 227 after the inner screw plug 100 is screwed into the outer screw 200. Subsequently, when a reverse rotation force is applied, the inner screw plug 100 and the second inner thread 227 begin to be threadedly connected, in such a manner that the claw-shaped segment 222 expands to form a plurality of claw-shaped structures.

Further, the inner screw stem 120 extends out of the outer screw stem 220, and a lower end 122 of the inner screw stem 120 can be fixed with an osteoporotic site in the body.

A locking nut 400 and an operating rod 300 are also included; the outer nut 210 has a locking groove 211 provided thereon and has a locking thread 212 provided inside; and the operating rod 300 is disposed in the locking groove 211, and is locked up through a threaded connection between the locking nut 400 and the locking thread 212.

The locking nut 400 has a first wrench operating groove provided thereon, and is configured to be screwed into the outer nut 210 and connected to the locking thread 212 by using a tool. The first wrench operating groove is preferably hexagonal inside.

The inner nut 110 has a second wrench operating groove provided thereon, and is configured to be screwed into the outer screw 200 and threadedly connected to the corresponding thread by using a tool. The second wrench operating groove is preferably hexagonal inside.

As a preferred embodiment, the claw-shaped segment 222 is made of pure titanium, and the thread segment 221 is made of titanium alloy. The two ends have different materials and different hardnesses, and therefore, the claw-shaped segment 222 is divided into a plurality of parts along the strip-shaped grooves 226 to expand under a subsequent force to form a plurality of claw-shaped structures.

As a preferred embodiment, the plurality of strip-shaped grooves 226 are uniformly arranged on the claw-shaped segment 222 along an axial direction of the claw-shaped segment 222. Preferably, three strip-shaped grooves 226 are provided, and form a shape similar to a four-leaf clover after expansion.

The structure and implantation method of the claw-shaped pedicle screw fastener (clawScrew screw fastener) for osteoporosis in the present disclosure are specifically described below.

The clawScrew screw fastener consists of three parts.

The first part is a configuration having the inner screw plug 100 in the outer screw 200, and the inner screw plug 100 is responsible for expanding an outer claw-shaped mechanical structure of the screw fastener to increase the holding force of the screw fastener in a vertebral body.

The second part is a configuration that a tail of the outer screw 200 has 2 cm that has been surface spray processed with hydroxyapatite, so as to increase bone ingrowth and reduce screw loosening, displacement and pullout.

The third part is a configuration that the outer screw 200 is designed as a conical structure, an axial interior of the outer screw 200 has a gradually increasing diameter in a direction from the thread segment 221 to the outer nut 210, and a front end is designed to have an inner diameter of 3 mm and a pitch of 5 mm. For each additional turn of thread, the pitch is reduced by 0.1 mm, and the diameter of the inner shaft is increased by 0.05 mm. In this way, the inner core portion of the screw fastener is designed to show a thickening trend, which reduces the fracture caused by metal fatigue after the screw fastener is implanted.

Implantation Manner:

A pedicle screw canal is prepared by conventional techniques. After the screw fastener is implanted, the operator uses a special inner screw plug wrench to screw in the screw plug. When the inner screw plug is screwed into the claw-shaped segment, the claw-shaped segment is continuously expanded as the screw plug is screwed in, and the space in the outer layer of the screw fastener is gradually filled by the central screw plug. During this process, it is necessary to monitor the expansion of the screw fastener in the vertebral body under fluoroscopy.

It should be noted that, in the description of the present disclosure, the terms "first", "second", etc. are only used for the purpose of description and to distinguish similar objects, and there is no chronological order between the two, nor can they be construed as indicating or imply relative importance.

Also, in the description of the present disclosure, unless otherwise specified, "plurality" means two or more.

It should be understood that the above description is for purposes of illustration and not limitation. From reading the above description, many embodiments and many applications other than the examples provided will be apparent to those skilled in the art. The scope of the present teachings should, therefore, not be determined with reference to the above description, but should instead be determined with reference to a full scope of the attached claims and equivalents thereof. For all purposes, the disclosures of all articles and references, including patent applications and publications, are incorporated herein by reference. The omission of any aspect of the subject matter disclosed herein in the attached claims is not intended to disclaim such subject matter, nor should be construed as the applicant not contemplating such subject matter as part of the disclosed subject matter.

What is claimed is:

1. A claw-shaped pedicle screw fastener for osteoporosis, comprising:

an outer screw comprising an outer nut and an outer screw stem, wherein a through hole is defined in and penetrates through the outer nut and the outer screw stem, the outer screw stem has a thread segment, a claw-shaped segment, and a conical segment that are provided on outside of the outer screw stem, the thread segment has a first inner thread provided inside, the claw-shaped segment has a plurality of strip-shaped grooves provided thereon and being in communication with the through hole, and the claw-shaped segment is smooth inside; the conical segment has a second inner thread provided inside; the claw-shaped segment is made of deformable metal; the thread segment has a first outer thread provided thereon, and a thread direction of the first inner thread is opposite to a thread direction of the second inner thread; and a thread direction of the first outer thread is the same as the thread direction of the second inner thread; and an inner screw plug comprising an inner nut and an inner screw stem, wherein the inner screw stem is inserted into the through hole, the inner screw stem has a second outer thread provided thereon, the second outer thread of the inner screw stem is connected to the first inner thread, and the second outer thread is configured to have an interference with the second inner thread under an action of a twisting force provided by the inner screw stem to twist and expand the claw-shaped segment.

2. The claw-shaped pedicle screw fastener for osteoporosis according to claim 1, wherein the outer screw stem is a conical structure, and the first outer thread has a decreasing pitch and an increasing thread diameter in a direction from the thread segment to the outer nut.

3. The claw-shaped pedicle screw fastener for osteoporosis according to claim 1, wherein the first outer thread has a hydroxyapatite spray coating on a tail thereof.

4. The claw-shaped pedicle screw fastener for osteoporosis according to claim 1, wherein the inner nut has a second wrench operating groove provided thereon.

5. The claw-shaped pedicle screw fastener for osteoporosis according to claim 1, wherein a length of the inner screw stem is equal to a length of the outer screw stem minus a length of the second inner thread.

6. The claw-shaped pedicle screw fastener for osteoporosis according to claim 1, further comprising an operating tool comprising a locking nut and an operating rod, wherein the outer nut has a locking groove provided thereon and a locking thread provided inside; and the operating rod, when in use, is disposed in the locking groove, and is locked up through a threaded connection between the locking nut and the locking thread.

7. The claw-shaped pedicle screw fastener for osteoporosis according to claim 6, wherein the locking nut has a first wrench operating groove provided thereon.

8. The claw-shaped pedicle screw fastener for osteoporosis according to claim 6, wherein the operating rod is axially perpendicular to the outer screw.

9. The claw-shaped pedicle screw fastener for osteoporosis according to claim 1, wherein the claw-shaped segment is made of pure titanium, and the thread segment is made of titanium alloy.

10. The claw-shaped pedicle screw fastener for osteoporosis according to claim 1, wherein the plurality of strip-shaped grooves is uniformly arranged on the claw-shaped segment along an axial direction of the claw-shaped segment.

* * * * *